United States Patent
Pullen

Patent Number: 5,995,908
Date of Patent: Nov. 30, 1999

[54] INTEGRATED FIELD MODELING SYSTEM

[75] Inventor: Margaret I. Pullen, P.O. Box 3207, Evergreen, Colo. 80439

[73] Assignee: Margaret I. Pullen, Aspen, Colo.

[21] Appl. No.: 08/272,667

[22] Filed: Jul. 11, 1994

Related U.S. Application Data

[63] Continuation-in-part of application No. 07/970,300, Dec. 28, 1992, abandoned, which is a continuation-in-part of application No. 07/631,736, Dec. 18, 1990, abandoned, and application No. 07/746,037, Aug. 15, 1991, abandoned, each is a continuation-in-part of application No.07/585,892, Sep. 20, 1990, abandoned.

[51] Int. Cl.$^6$ ....................................................... G06F 17/00
[52] U.S. Cl. .............................................. 702/27; 702/19
[58] Field of Search .................................... 364/496, 497, 364/499, 578; 395/500; 702/19, 22, 27

[56] References Cited

U.S. PATENT DOCUMENTS

| | | | |
|---|---|---|---|
| 4,704,692 | 11/1987 | Ladner | 364/578 |
| 4,881,175 | 11/1989 | Ladner | 364/578 X |
| 4,908,773 | 3/1990 | Pantoliano et al. | 702/138 |
| 4,939,666 | 7/1990 | Hardman | 364/578 X |
| 4,946,778 | 8/1990 | Ladner et al. | 435/69.6 |
| 5,353,236 | 10/1994 | Subbiah | 364/578 X |
| 5,418,944 | 5/1995 | Di Pace et al. | 702/27 X |
| 5,420,805 | 5/1995 | Still et al. | 702/27 X |
| 5,424,963 | 6/1995 | Turner et al. | 364/578 |
| 5,434,796 | 7/1995 | Weininger | 364/578 |

OTHER PUBLICATIONS

Marcus et al., "Electron transfers in chemistry and biology," Elsevier Science Publishers B.V., 1985, pp. 265–276.

Berry, "Quantal phase factors accompanying adiabatic changes," Proc. R. Soc. Lond. A 392, 1984, p. 45–57.

Marcus et al., "Theory of Electron Transfer Reactions and Comparison with Experiments," Photoprocesses in Transition Metal Complexes, Biosystems and Other Molecules, Experiment and Theory, 1991, pp. 49–88.

D.D. Frantz et al., Lewis Electronic Structures as the Large–Dimension Limit for $H_2^+$ and $H_2$ Molecules, Department of Chemistry, Harvard University, Jul. 11, 1988

Shyh–Gang Su et al., "Picosecond Fluorescence Dynamics of p–Dimethylaminobenzonitrile in Alcohol Solution," SPIE vol. 910 Fluorescence Detection II (1988).

*Primary Examiner*—William A. Cuchlinski, Jr.
*Assistant Examiner*—Edward J. Pipala
*Attorney, Agent, or Firm*—Birch, Stewart, Kolasch & Birch, LLP

[57] ABSTRACT

Computer modeling of charge transfers, i.e, chemical reactions is accomplished by modeling the reaction of electron donor and acceptor moieties of reactive chemicals one reaction step at a time. In the modeling process the moiety (donor/accepter atoms) position and their desired quantum values per reactant moiety are input into the computer using literature or other predetermined data. The spherical coordinate of the moieties are calculated from time zero to reaction completion constrained by the formula $$\tilde{G} = \lambda/4[1 + \tilde{G}(0)/\lambda] \qquad (2)$$

Where the parameters are defined above.

The spatial position of the initial product and any additional reactant, e.g., in polymeric, etc., reactions is similarly calculated until the reaction is terminated.

6 Claims, 3 Drawing Sheets

FIG.3

```
┌─────────────────────────────────────────────────────────────┐
│  A Method for Identifying and Synthesizing a First Molecule │
│  in a Bio-Molecular Binding Event, Comprising the Steps of; │
└─────────────────────────────────────────────────────────────┘
                              │
┌─────────────────────────────────────────────────────────────┐
│     Assigning to an Electron Donor Atom of a Second Molecule │
│           a Fixed Geometric Location Within Generalized      │
│  Dimensionally Scaled Coordinates Adjacent the Putative Nucleus │
└─────────────────────────────────────────────────────────────┘
                              │
┌─────────────────────────────────────────────────────────────┐
│   Assigning to an Electron Acceptor Atom a Fixed Geometric  │
│         Dimensionally Scaled Coordinates at Time Zero        │
│            and at a Distance Exceeding Van der Waals         │
│         Distance Between the Donor and Acceptor Moieties     │
└─────────────────────────────────────────────────────────────┘
                              │
┌─────────────────────────────────────────────────────────────┐
│       Utilizing Formula $G^* = \lambda/4\ (1 + G(0)/\lambda)(2)$ │
│            Where $\lambda$ is Nuclear Reorganization Energy  │
│   and G is Standard Free Energy of Reaction to Limit Distance│
│          of Transfer of Moment of Impact of the Acceptor,    │
│ Wherein the Donor is Considered to be Fixed with Respect to Coordinate Origin │
│  in a Charge Transfer Reaction Between the Fixed Donor and the Acceptor │
└─────────────────────────────────────────────────────────────┘
                              │
┌─────────────────────────────────────────────────────────────┐
│ Identifying Said First Molecule by Deterministic Mathematical│
│       Inversion of Relationship with Said Second Molecule    │
└─────────────────────────────────────────────────────────────┘
                              │
┌─────────────────────────────────────────────────────────────┐
│              Synthesizing Said First Molecule                │
│          Based on Data Obtained From Above Steps             │
└─────────────────────────────────────────────────────────────┘
```

INTEGRATED FIELD MODELING SYSTEM

The present application is a Continuation-in-Part application of Ser. No. 07/970,300, filed Dec. 28, 1992, which is a Continuation-in-Part application of Ser. Nos. 07/631,736, filed Dec. 12, 1990 and 07/746,037, filed Aug. 15, 1991 which are Continuation-in-Part applications of Ser. No. 07/585,892, filed Sep. 20, 1990, all abandoned. The contents of all of the above parent applications are incorporated by reference herein in their entirety.

FIELD OF INVENTION

This invention relates to a programmed computer and computer based method for modeling atomic and molecular dynamics. More specifically, this invention is designed to facilitate the modeling of biological reaction systems at least one charge donor and at least one charge acceptor in order to predictively model electron transfer reactions.

BACKGROUND OF INVENTION

There typically are several methods for developing biological reaction systems for diagnostic and therapeutic purposes. A large industry has developed which is involved in the isolation, identification, purification development and production of naturally occurring compounds.

For many years efforts have been directed to the development of therapeutic or diagnostic reagents which are based purely on trial and error experimentation. On the other end of the research spectrum from this approach is to model or "design" therapeutic or diagnostic agents. This is possible due to the abundance of biological information that is now available on the molecular level. Since the advent of AIDS the search for better approaches has increased.

A series of U.S. patents have been issued that describe a modeling method for utilization in bimolecular reaction. See, e.g., U.S. Pat. No. 4,939,666 of Hardman, and U.S. Pat. Nos. 4,946,778; 4,908,773; 4,881,175; 4,8532,871; and 4,704,692. The '666 patent of Hardman describes what is known as the CHARMM model.

The differences between the present invention and CHARMM rest on how the dynamics of molecules are generated. CHARMM and analogous systems, apply Langevin Dynamis and Stochastic Boundary Dynamis or similar methods to predict the motions of molecules. These principles, and the equation used to simulate these principles, apparently assume the environment of a molecule randomly haphazardly disturbs that molecule.

In the present invention the premise for biological systems is that the environment of a molecule precisely and very specifically may interact with the given molecule. The bit transfer mapping scheme is based on empirical experimental data to characterize the motions of molecule. The specific set of biochemical events are identified and it is assumed that the relevant stable elementary particle that transfers during a given chemical reaction, such as the redox event, induces the dynamic of a molecules reaction.

SUMMARY OF THE INVENTION

The process steps broadly speaking are:
a assigning to an electron donor a fixed geometric location within spherical coordinates adjacent the putative nucleus,
b assigning to an electron accepter a fixed geometric location and where desirable, quantum conditions with the spherical coordinates at time zero and at a distance exceeding the Van der Waals distance between the donor and acceptor chemical moieties,
c recalculate the position of each of the donor and acceptor periodically during the movement of he donor and acceptor from their original site to the site of the charge transfer using in part the constraining formula:

$$\dot{G}(*) = \lambda/4(1+\dot{G}(0)/\lambda) \qquad (2)$$

where $\lambda$ is the nuclear reorganization energy and G is the standard free energy of the reaction.

d applying linear superpositioning to model the geometric spatial and/or energy changes during the reaction to determine the most likely spacial relationship between the reacting chemical moieties and/or energy transfer point.

The computer can be used to provide a visual representation of the molecules and these reacting moieties as they approach each other in the reaction environment, e.g., solvents, co-solvents, etc.

Calculation of the energy transfer point from the computer or mathematical viewpoint occurs when nuclear configurations of the atom(s) of the reacting moiety are at or near that point where the total potential energy of the reactants and surrounding medium is equal to that of the products and surrounding medium.

Once the initiation of a multi-step reaction is calculated, the process, described above can be repeated as many times as necessary to complete the chemical process, e.g. in the modification of a genome.

Other data can be included in the initial and subsequent computation of the spacial relationships, e.g., electron position and nuclear spin components, and charge magnitudes.

BRIEF DESCRIPTION OF THE DRAWINGS

The objects of the present invention will become more apparent by reference to the following figures of the drawings wherein:

FIG. 3 is a flowchart that applies the present invention to construction of a computer with attached instrumentation to synthesize the first molecule.

Figure 1:
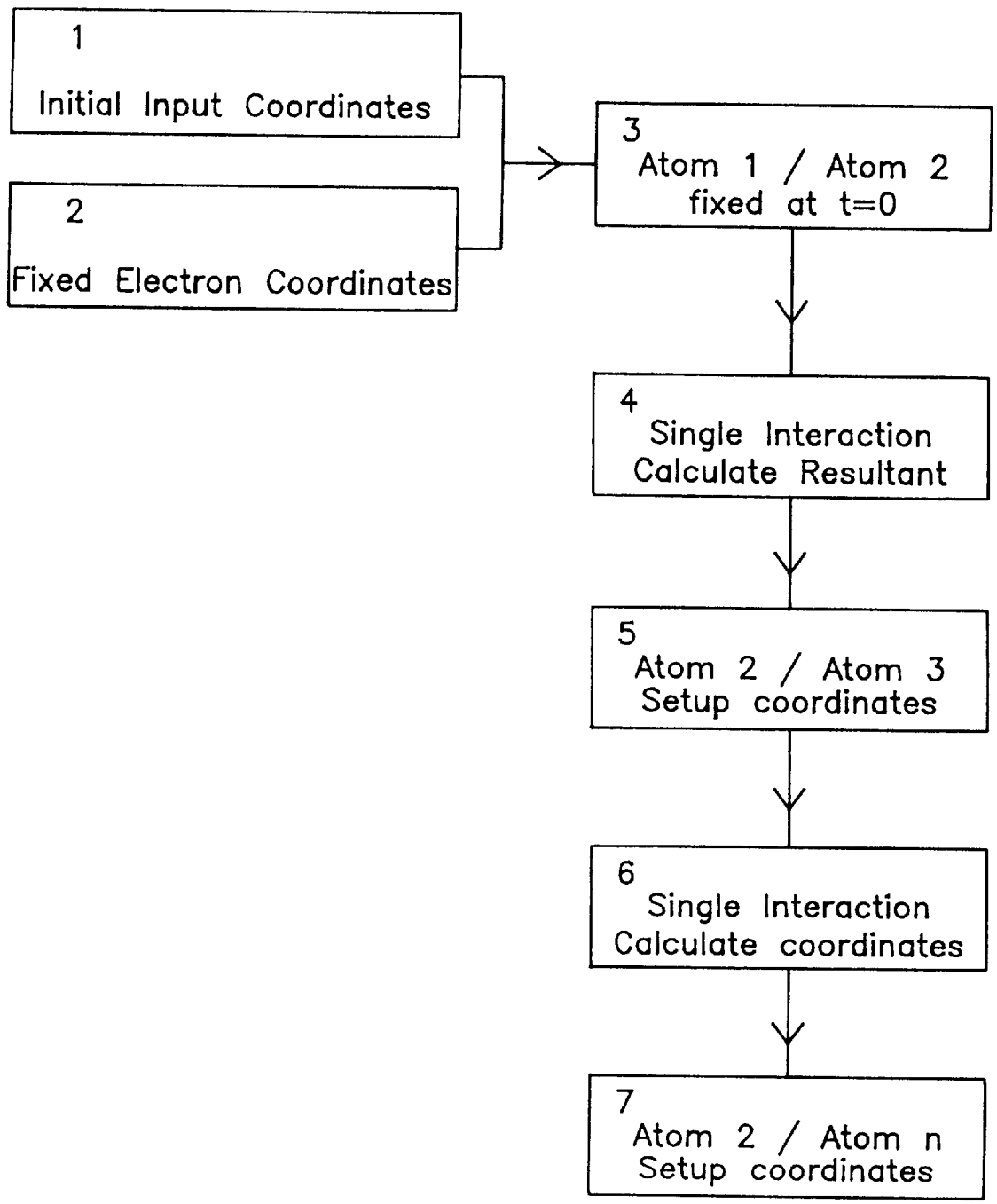
FIG. 1 is a flow chart of the steps required for the calculation of the initial spatial configuration of he system and chemical moieties.
Figure 2:
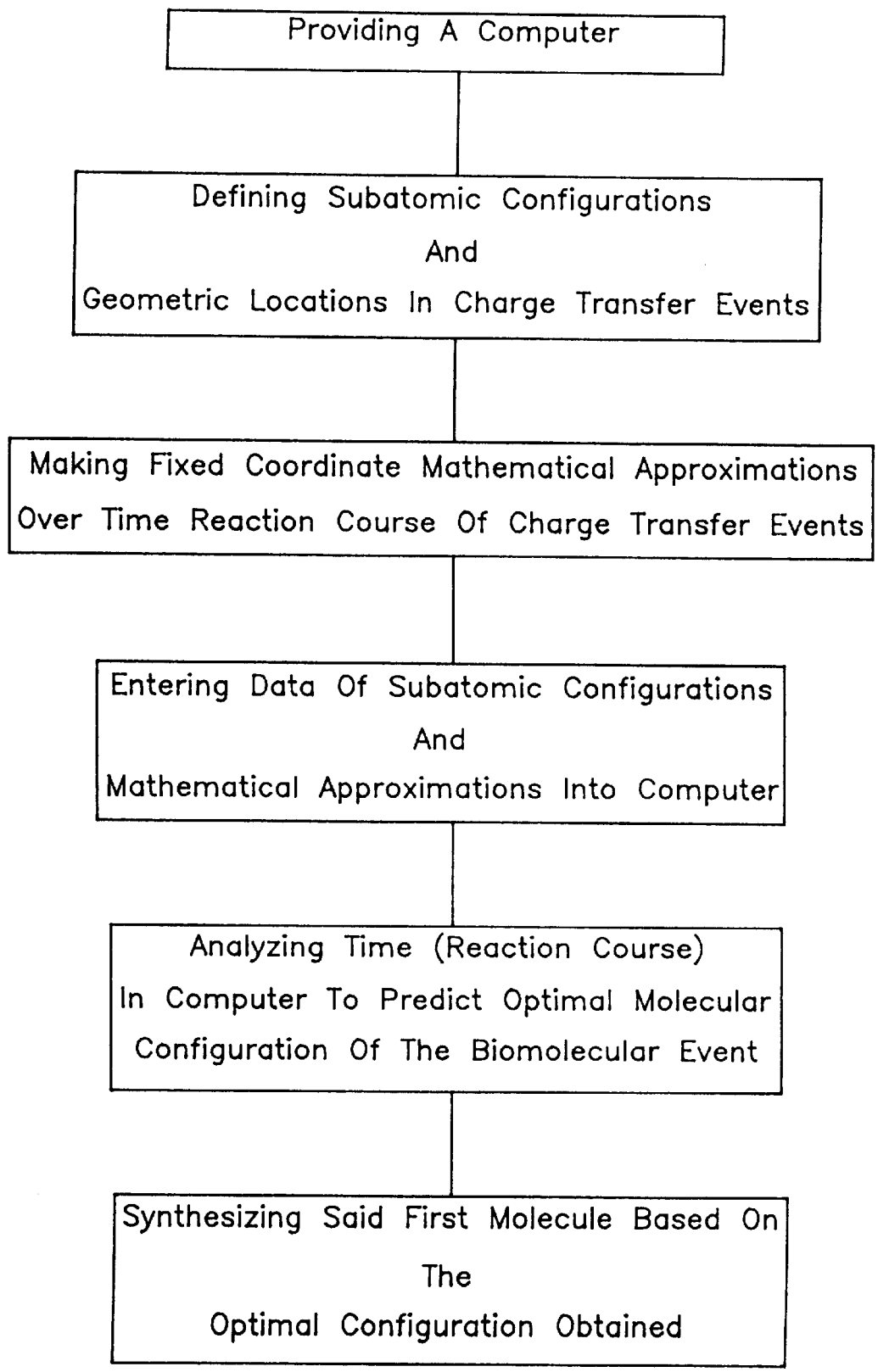
FIG. 2 is a flowchart generally illustrating the method of synthesizing a molecule according to the present invention.

The initial input coordinates (1) provide the (x,y,z,) and time axes for the spherical referencing. The fixed electron coordinates (2) are established by transforming the coordinates of dimensional scaling {see Herschbach, "Lewis Electron Structures as the large-Dimensional Limit for H(*)2 and H(2) Molecules", Chem. Phy. ,126, (1988) p 59–71.} to spherical coordinates {CRC Standard Mathematical Tables, 27, Beyer,H.B,ed., p 210} and then to Eulerian angles {Landau, L.L., Classical Mechanics, 3rd Ed., Pergamon Press, (1982), Chapter 6, sec. 35., p 110}. Then each of the coordinates of (1) and (2) are input into the computer data bank for atoms (1) and (2) at time zero (3). Quantum input is introduced by matrix calculations {see Hildebrand, H., Methods of Applied Mathematics, 2ed, Prentice Hall (1965) chapter 1}. The calculations (4) are made using the previously identified formula to establish boundary conditions, {see Marcus, below}.

In reactions where there are a sequence of reactions, the resultant coordinates of step (4) are used in the calculation of the rest interaction between atom (2) and atom (3) through n with the understanding that the reaction of atoms (1) and (2) creates a product with then a known orientation. This resultant then provides known orientation which provides input data for atom (3) of step (5). The reactant having the moiety of atom (2) continues to react with products of atom (3) through atom n as the reaction progress to its end point (7). The simple interaction resultant (6) is obtained for each of these products.

GENERAL DISCUSSION OF THE INVENTION

With present invention, biological reactions may be modeled to effectively design therapeutic or diagnostic agents. The method or system of the present invention involves the utilization of fixed coordinate mathematics which can be employed to analyze a molecular event in a unique manner.

In the primary examples described herein, a charge transfer event is mapped or modeled. The charge transfer event leads to an atomic event (integrated fields), which in turn leads to the molecular event. Rather than viewing the manifestations of the molecular event, the modeling focusses on the initial event which initiates the chain response and subsequent event which continue the reaction to its endpoint.

The modeling will generally be preformed on discrete charge transfer events separately and then by applying linear superposition to modeling each site, the chain response of one molecule in isolation and then adding them to define the entire molecule implemented on, e.g. MIMD, parallel processing computer recognizing that the complex molecular event may involve the accumulative effects of a larger number of simultaneous or near simultaneous molecular events.

The charge transfer modeling is preformed utilizing the mathematics of dimensional scaling, the transforming to Cartesian spherical coordinates and then transforming to Eulerian angles. According to this theory, or modeling protocol, the electrons of an atom have a fixed geometric location at any given point in time. A ground state charge transfer event is modeled by viewing the event at t=0, at intermediate times and after the transfer event has been completed. The effect of the geometric orientation of the acceptor atom can be studied due to the utilization of the fixed electron location mathematics. By combining the information obtained from the individual charge transfer events, it is possible to design molecules containing the optimal orientation for effecting the desired molecular event.

DETAILED DESCRIPTION OF THE PREFERRED EMBODIMENT

The first stage of the system or method of the present invention is best understood by reference to the application of the model to a single charge transfer event. This state of analysis is referred to in computerease as bit transfer mapping.

The bit transfer map includes a mathematical analysis of the charge donor, the charge (either a proton or an electron), and the charge acceptor. The elements of the system are examined at a variety of time points including t=0 (before charge transfer begins) at t=f (after charge transfer is completed) and various t=i (intermediate times). In each discrete time frame, the state of each of the elements is numerically framed in a two dimensional coordinate. The elements are characterized both geometrically and according to their atomic states.

The use of bit transfer mapping is employed to provide predictability to, e.g., DNA dynamics being studied, one gene at a time. Of course, the use of bit transfer mapping could equally well be applied to the analysis of any number of other molecular events. From the reference provided by bit transfer mapping and charge transfer events, molecular bonds may be formed, broken, or twisted.

The approach of two molecules leading to a molecular event is influenced by three-dimensional dynamics of the starting material as well as the ultimate event that is to occur. From the dynamic three-dimensional geometry of the molecules, the electrostatic field of the molecules, the electrostatic field of the molecules, the electrostatic field of the molecules are defined. The electrostatic fields of the molecules as they approach prior to a molecular event describe the interface between the reactant molecules; e.g., the approach of a molecule that binds to a gene sequence and the specific gene.

A simple molecular event that can be examined to help explain the system of the present invention is the isomerization of stilbene. Trans-stilbene will be isomerized to cis-stilbene under certain reaction conditions. Although the ground state energies of the cis- and trans-molecules are relatively similar, a large energy barrier must be overcome to accomplish the bond breaking/rotation event.

The presence of an electron source, the transformation can occur with or without electron tunneling. The energy required in order to achieve the transformation without tunneling is commonly referred to as the "reorganization energy". See Marcus et al., *Biochem. Biophys. Acta*, (1985) 811, p 265–322. This represents the classical outside to inside manner of viewing the molecular event.

According to the method of the present invention. The electron transfer event is examined. The charge transfer event leads to an atomic event, which in turn leads to the molecular event. The charge transfer event is the approach of an electron to the trans-stilbene molecule.

According to the method of the present invention, the atomic stilbene that accepts the electron can be modeled to determine the optimal configuration for acceptance of the electron. The bit transfer mapping of this interaction provides that electron donor and acceptor atoms each be viewed at discrete time periods and their atomic states and geometric locations fixed. The charge transfer event acts as a catalyst to initiate the subsequent atomic and molecular events.

Traditional mathematical formulations of the electron location around a nucleus as used herein are represented by quantum mechanical calculations. The result is a probability that the electron might be at a particular location relative to the nucleus of the atom.

The mathematics of dimensional scaling represent an alternative approach to the formulation of atomic geometries. Dimensional scaling is a formulation or approach known to those skilled in the are, and this described in Herschbach, *Chemical Scripta* (1987) 27, p 327–347; Loeser, *J Chem Phys.*, (1987), Vol 86, p 5635–3646, each of which are specifically incorporated herein by this reference. According to this mathematical model, the location of electrons can be "fixed" relative to the nucleus; i.e., the distance of the electron from the nucleus and the angle of the electrons with respect to a nucleus are fixed. {The inventor uses the s state, zero angular momentum, electrons as fixed electrons}. The differences and similarities between the quantum mechanical and dimensional scaling approaches are illustrated in FIG. 3. The use of dimensional scaling, although adaptable to higher state reactions, is particularly well suited for the evaluation of ground state reaction dynamics.

It is assumed that the electron transfer at a subsequent time zero is a linear event—without significant dispersion. See Flemming et al Physics Today, (1990) May p. 36–43. The energy necessary to align the donor molecule into the appropriate geometric state to accept the electron is analogous to the classical concept of the reorganization energy. See Marcus supra; and McLendon, *Accts. Chem. Res.*, (1988) 21, p 160–167 incorporated herein by this reference.

The key element of the bit transfer mapping is the analysis of the rotation about the axis of the nucleus of the acceptor atom required to accept their incoming electron. The conservation of energy and momentum require secondary objects bonded to the acceptor to adjust themselves to accommodate the new alignment of the acceptor. The charge transfer, from the perspective chosen, initiates the charge-to-atomic-to-molecule event, i.e., the chain response.

The energy required to rotate the acceptor atom about its nuclear axis is porportational to G. G in turn is equal to $\lambda$, which is the classically defined reorganization energy, when no tunneling is required.

The Charge transfer modeling is performed by transforming the coordinates of dimensional scaling to spherical coordinates and then to Eulerian angles. The closer the nuclear orientation of the acceptor is aligned to the path of the incoming electron, the longer the distance the acceptor may be from the donor atom for charge transfer to occur.

The application of the bit transfer mapping to the design of desirable therapeutic of diagnostic agents is accomplished by the addition of a plurality of maps to model the bio-circuit. Since in many, if not most, bimolecular events a significant number of charge transfer events must occur, it is possible to determine the proper acceptor or donor alignments of group atomic events. This knowledge can be applied by one ordinary skill in the art without undue experimentation to construct molecules to interact in the desired manner with the biological system--knowing the optimal nuclear alignment for reducing the electron reorganization energy.

Because an electron, for example, is considered fixed with respect to the nucleus of the atom, via Dimensional Scaling or the like, exact dynamics can be quantified. Typically, these events may happen via quantum ground state electronic exchanges.

The second sub-component distinction is the application of Dimension Scaling, or an analogous theory, of quantum characterization of the bound electron, rather than the traditional orbital electron method. The method of the present invention considers that certain electrons are fixed with respect to their respective nucleus. By constraint of the bound electron's location, (and the proton, or a hole) one is able to quantitatively model the relative rigid body type motions of an atom, then subsequently and contiguously the motion of the molecule of which that atom is a component.

The empirical data from X-ray crystallography, and other experimentation, is dead, that is used to initiate equilibrium, molecular parameters as done in the already existing codes.

This bio-computer can be accurately characterized by mapping out the individual currents and circuits that bit transfers map into. Current experimental technologies determine these transfers. (Such as those used to produce, "Long-distance Electron Transfer in Proteins and Model System, George McLendon, *Accounts of Chemical Research*, 21,p 160,(1988). By transformation to a numerical reference frame, composed of just the bits (electron, holes, protons), switching sites, for each time step, the bio-circuitry of the living cell can be simulated with avoidance of "molecules" per se.

The method used is very straight forward. One after another of the biochemical reactions are arranged as they occur within the cell. By mapping the bit transfers that connect this set of biochemical events one can decipher the higher level language of the cell. By comparison of a good vs. erroneous set of bit transfer maps for a given biological process on the, e.g., DNA/Binding molecule interface, it is possible to recognize required sites in which to place or remove the structural moieties at the right site at the right time to create molecules correcting viral disease, genetic disorders, and to control advantageously regeneration mechanisms.

Tools utilized to mathematically characterized the bio-computer and bit transfers include: a reduced conduction band concept from solid state theory, n & p junctions, an increase in detail correlation function theory, a dimensional scaling or analogue theory, and rigid body dynamics.

Contrary to other approaches to model the dynamics of molecules, the present invention creates a "unified field method" of bio-systems. Electron and proton dynamics are connected with atomic dynamics and the particles and events can be represented by a bit transfer map which is then used to program a computer. Electron and proton dynamics are connected with atomic dynamics and utilized together to identify first the atom's dynamics, then to the molecule's dynamics, and lastly to the bio-processing of the entire cell. A complete picture of the biosystem is presented.

The maps are placed continuously together over each girded area, of the DNA/binding site, or over the entire gene, or over the entire cell and then over the entire severed area of a limb or spinal cord site, depending upon the application and medical problem we are to resolve and correct.

In one embodiment of the invention, a study of the AIDS model has been chosen. Extensive studies have been conducted and continue to be done, providing the latest understanding of the system which we are using as a model. For example, extensive information is available on the HIV-I and its known modes of action. The entire HIV genome has been sequenced, therefore its biological processes can be determined, with the addition of application of this technology. See, e.g. R. Yarchaon and S. Broder, "Immunology of HIV Infection", in *Fundamental Immunology*, 2d ed., Paul, William E., ed, Raven Press Ltd., New York (1089), specifically incorporated herein by this reference.

The HIV has a glycol-protein on its surface which binds to a specific cell receptor site. This molecule then is able to penetrate the CD4 cell. Once into the cell the virus "uncoats" and its nucleic acid is set free to be reverse transcribed into DNA. The HIV is then integrated into the host genome. According to one embodiment of the present invention, one can fuse the gene for the cell surface receptor cognate molecule to an altered host pol II or any other facilitating protein gene. The altered host pol II or any other facilitating protein is the intercept molecule. This intercept molecule binds to specific promoter sites of the genome in place of the natural pol II or any other facilitating protein. The altered pol II or any other facilitating protein will not transcribe, then the altered pl II or any other facilitating protein cannot bind nor transcribe the genes. Viral proteins cannot be made. The virus is switched off forever.

The DNA promoter site charge structure and the pol II or any other facilitating protein binding site charge structure are anti-sense complementary. Once we know the charge composition over the binding region on the DNA then, we automatically know the charge composition of the binding molecule over its binding region of the DNA. Therefrom the necessary target drug software templates are produced.

All the technologies for these procedures are well known to those skilled in the art. {see, e.g., Stefano et al., *J. Biol. Chem.*, 255, 0 10223–10430 (1980); Chan et al., *J. Biol Chem.*, 265, p. 409–4097 (1990); Siegelle et al., *J. Mol. Biol.*, 206, p 591–603 (1989); and Hynes et al., *Nature* 339, 0 73–76 (1989)

I claim:

1. A computer assisted method for identifying and synthesizing a first molecule in a bimolecular binding event, comprising the steps of:
   (a) numerically defining the subatomic configuration and geometric locations involved in charge transfer events on a subatomic level of a second molecule using fixed coordinate mathematical approximations over the time/reaction course of the charge transfer event;
   (b) entering data obtained in step (a) into a computer that is programmed to analyze the time/reaction course to predict the optimal molecular configuration of the bimolecular event; and
   (c) synthesizing said first molecule based on the optimal molecular configuration obtained in step (b).

2. The method of claim 1, wherein said first molecule is a protein.

3. The method of claim 1, wherein said second molecule is a nucleic acid.

4. A computer comprising a software program that carries out the instructions according to claim 1.

5. A method for identifying and synthesizing a first molecule in a bimolecular binding event, comprising the steps of:
   (a) assigning to an electron donor of a second molecule a fixed geometric location within generalized dimensionally scaled coordinates adjacent the putative nucleus;
   (b) assigning to an electron acceptor a fixed geometric location with the generalized dimensionally scaled coordinates at time zero and at a distance exceeding Van der Waals distance between the donor and acceptor moieties;
   (c) utilizing formula $$G(*) = \lambda/4(1+G(0)/\lambda) \qquad (2)$$

where $\lambda$ is nuclear reorganization energy and G is standard free energy of reaction to limit distance of transfer of moment of impact of the acceptor, wherein the donor is considered to be fixed with respect to coordinate origin in a charge transfer reaction between the fixed donor and the acceptor;
   (d) identifying said first molecule by deterministic mathematical inversion of relationship with said second molecule; and
   (e) synthesizing said first molecule based on data obtained from steps (a) to (d).

6. A computer comprising a software program that carries out the instructions according to claim 5.

* * * * *

UNITED STATES PATENT AND TRADEMARK OFFICE
CERTIFICATE OF CORRECTION

PATENT NO. : 5,995,908

DATED : November 30, 1999

INVENTOR(S) : Margaret I. Pullen

It is certified that error appears in the above-identified patent and that said Letters Patent is hereby corrected as shown below:

On the title page, Item [75] should read:

Margaret I. Pullen
P. O. Box 1551
Aspen, CO 81612

Signed and Sealed this

Fifteenth Day of August, 2000

*Attest:*

Q. TODD DICKINSON

*Attesting Officer*  *Director of Patents and Trademarks*